United States Patent [19]
Christoudias

[11] Patent Number: 6,019,770
[45] Date of Patent: Feb. 1, 2000

[54] VERSATILE ENDOSCOPIC RETRIEVAL BAG

[76] Inventor: George C. Christoudias, 17 Lower Cross Rd., Saddle River, N.J. 07548

[21] Appl. No.: 09/163,213

[22] Filed: Sep. 29, 1998

Related U.S. Application Data

[60] Provisional application No. 60/067,046, Dec. 4, 1997.

[51] Int. Cl.[7] ................................................. A61B 17/24
[52] U.S. Cl. ........................ 606/114; 604/408; 604/403
[58] Field of Search ................................... 606/114, 110;
604/408, 342, 339, 403, 322; 383/42; 24/455;
292/256; 220/315; 248/311.2; 43/7, 134;
D8/354; 150/150, 100; 600/213, 228, 224

[56] References Cited

U.S. PATENT DOCUMENTS

| | | | |
|---|---|---|---|
| 2,016,551 | 10/1935 | Landis | 150/29 |
| 3,189,253 | 6/1965 | Mojonnier | 229/66 |
| 5,931,777 | 8/1999 | Sava | 600/213 |

*Primary Examiner*—Michael Buiz
*Assistant Examiner*—Anthony S. King
*Attorney, Agent, or Firm*—Richard A. Joel, Esq.

[57] ABSTRACT

A versatile endoscopic retrieval bag system comprises a collapsible bag and a cooperating manipulating instrument or grasper. The two layer bag comprises an outer layer waterproof plastic bag and an inner layer mesh plastic bag which is rolled between two sides of a firm plastic rim which includes a hinge or discontinuity at the center and each end of each rim to permit bending of the rim at four points. The limbs of the manipulating instrument fit snugly onto the rim at one end up to the discontinuity. In use, the manipulating instrument is activated causing the rim to assume a substantially square, open configuration with the collapsible bag extending outwardly therefrom within a body cavity to receive various body organs or tissues.

10 Claims, 3 Drawing Sheets

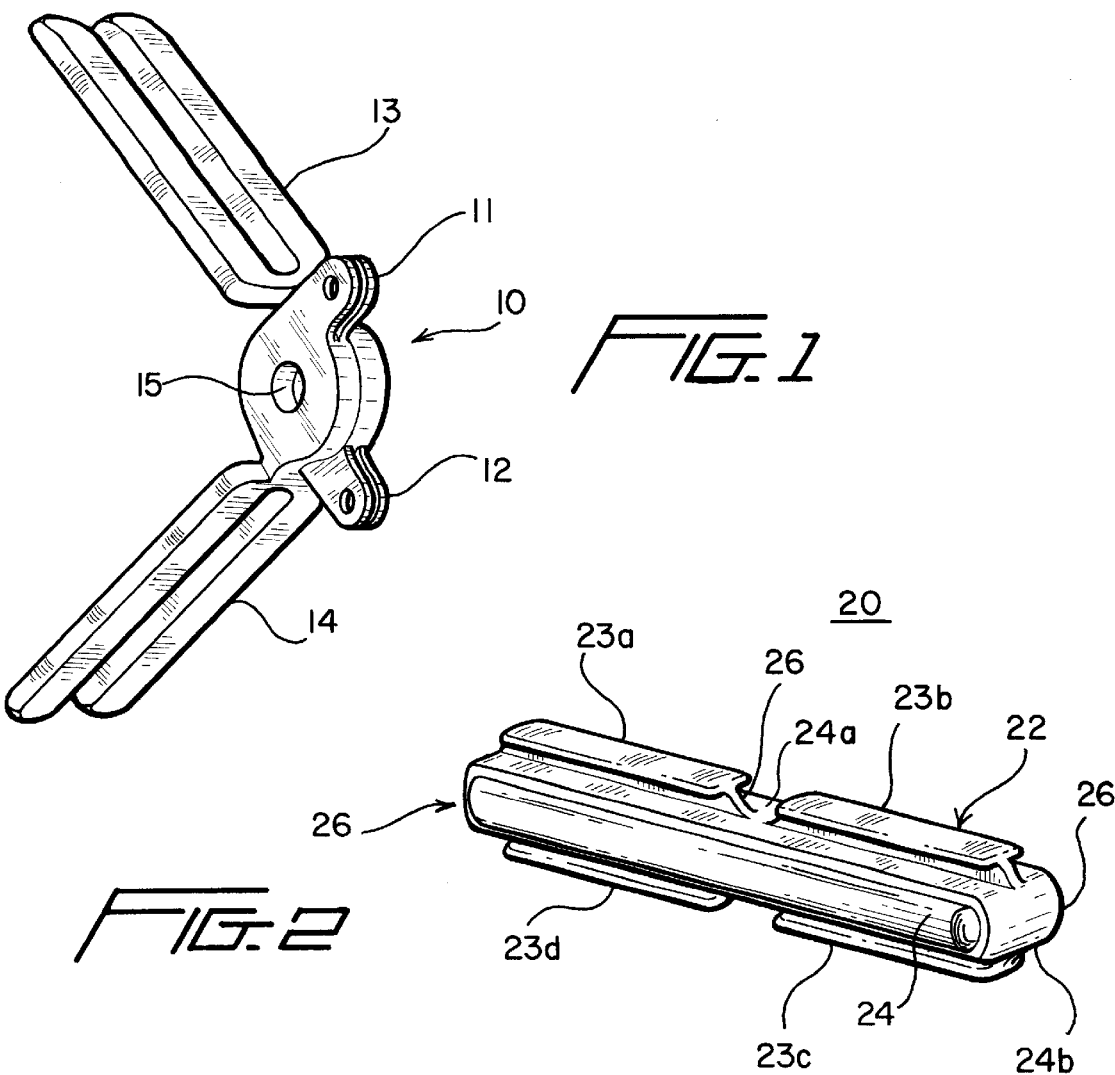
FIG. 1
FIG. 2
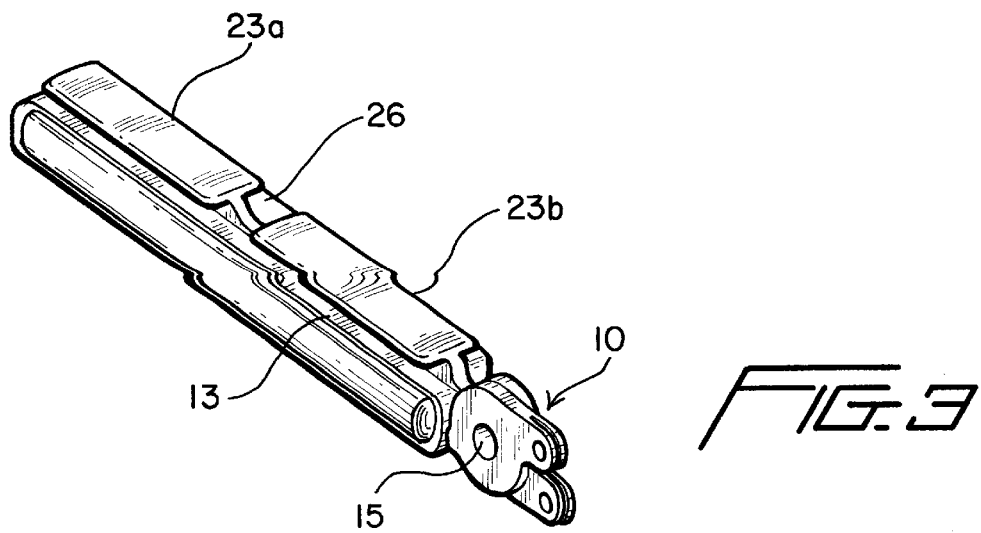
FIG. 3

VERSATILE ENDOSCOPIC RETRIEVAL BAG

This application claims benefit under provisional application Ser. No. 60/067,046 filed Dec. 4, 1997.

BACKGROUND OF THE INVENTION

Endoscopic surgery continues to gain ground as the predominant modality for certain abdominal operations such as cholecystomy and appendectomy. It is also used in thoracoscopy for partial or total lung lobectomy.

In all procedures that involve removal of an organ such as gall bladder, appendix, colon, spleen, ovary, lymph nodes, lung, etc., there is a need for a retrieval bag that can carry the organ from the body cavity to the outside. All these organs are of different size and volume and would require retrieval bags of a different size corresponding to their dimensions. Also, on occasion, there could be a spill of stones from the gall bladder which would necessitate sequential stone retrieval and placement into the bag.

The retrieval bag systems currently on the market generally involve totally disposable instruments and are of one certain size such as the Pleatman Sac of Circon-Cabot Surgical or the Endocatch of U.S. Surgical. One system, the Pleatman Sac has a continuously open mouth or opening that could allow the specimens entered into it to slip or fall out during retrieval of the bag from the body cavity. The Endocatch of U.S. Surgical has a purse string which once activated, tears the plastic bag off a metal spring and closes the bag permanently. The retrieving ability of the bag is terminated after closure of the bag.

The prior art includes U.S. Pat. No. 5,192,284 to Mark A. Pleatman which discloses a surgical collector and extractor for specimen removal through a cannula in a laparoscopic procedure. The device includes a flexible sac for collection purposes.

U.S. Pat. No. 5,190,555 to Wetter discloses a tissue collection device having a flexible sack activated by a drawstring. U.S. Pat. No. 5,176,687 to Hasson, et al relates to an apparatus for removing an internal mass with a membrane which assumes an expanded state.

Other patents of interest are U.S. Pat. Nos. 5,147,371 and 5,643,283 both of which disclose a collapsible pouch for collecting body parts for removal during surgery. None of the prior art patents disclose a device anywhere similar to the present invention.

The current invention addresses the need for versatility in retrieval dimensions as well as the ability to open and close the entrance to the retrieval bag at will, elements that are not present in the currently available retrieval bags.

Another element that is unique to the current invention is the fact that this instrument is comprised of two distinct parts, a reusable manipulating instrument and a disposable bag. This feature involves a sturdy, easy to handle manipulating instrument that can be used over and over again. A disposable bag of various sizes fits snugly onto the specially designed jaws of the manipulating instrument or grasper and is the only part that is disposable thereby providing a less costly and an environmentally friendly assembly.

Another feature that is also unique to the current invention is the fact that the retrieval bag is comprised of two layers, an outer water proof layer for the blood and body fluids, and an inner perforated layer to engage and separate the solid tissues and structures from the body fluids. This separation renders the removal of the bag from the body cavity easier as the bag contents are spread more evenly in the bag and are prevented from being bunched up at the bottom of the bag.

SUMMARY OF THE INVENTION

This invention relates to surgical retrieval bags and particularly to a versatile endoscopic retrieval bag.

The retrieval bag is utilized with a manipulating instrument comprising a laparoscopic grasper mechanism with specially designed grasping jaws which permit simultaneous activation of both limbs of said jaws. The jaws of the manipulating instrument are designed specifically to fit snugly onto the retrieval bag. The bag is also designed to mate with the jaws of the instrument.

The bag system comprises a collapsible plastic bag which is rolled or folded between and attached at its edges to opposing plastic rim portions of a firm structure. Each of the rim portions has a hinge or discontinuity at its center and both ends which permits the rim to bend at the center and both ends forming an entrance aperture into the bag. The rim bending is caused by activation of the manipulating instrument.

The first half of the rim portions attaches snugly onto the limbs of the manipulating instrument. Opening of each of the jaws or limbs to a 45° angle from the longitudinal axis of the instrument forces the retrieval bag to its maximum open position which forms a square opening and allows placement of the removed organ into the bag. Different sizes of bags can fit onto the manipulating instrument permitting use of the appropriate bag for the removal of specific organs.

As a further feature, the retrieval bag involves a two layer design comprising inner and outer bags. The outer bag comprises a waterproof plastic layer and the inner bag comprises a shorter and firm mesh layer which permits blood and fluids from the organs to drain into the outer waterproof bag. This separation of the solid of fluid parts of the tissues distributes their volume more evenly and prevents them from getting bunched up at the bottom of the bag. The more even distribution of the tissue volume within the bag renders the extraction of the bag through a small opening of the body cavity easier, safer and more expeditious Accordingly, it is an object of this invention to provide a new and improved endoscopic retrieval bag.

Another object of this invention is to provide a new and improved retrieval bag to remove organs or tissues of various sizes.

A further object of this invention is to provide a new and improved disposable organ retrieval bag which functions with a manipulating instrument to efficiently and effectively open and close at will about hinges to remove organs and or tissues during laparoscopic surgery.

A more specific object of this invention is to provide an organ retrieval bag having a two layer design and having a rim which expands upon activation by a manipulating instrument the limbs of which fit snugly onto the forward portion of the rim up to a hinge or discontinuity which facilitates bending of the flat rim and opening of the bag.

BRIEF DESCRIPTION OF THE DRAWINGS

The above and other objects and advantages of this invention may be more clearly seen when viewed in conjunction with the accompanying drawings wherein:

FIG. 1 is a perspective view of the manipulating instrument or grasper with the jaws in an open position;

FIG. 2 is a perspective view of the retrieval bag in a closed position;

FIG. 3 is a perspective view of the bag and manipulating instrument in a closed position;

DETAILED DESCRIPTION OF THE INVENTION

Figure 4:
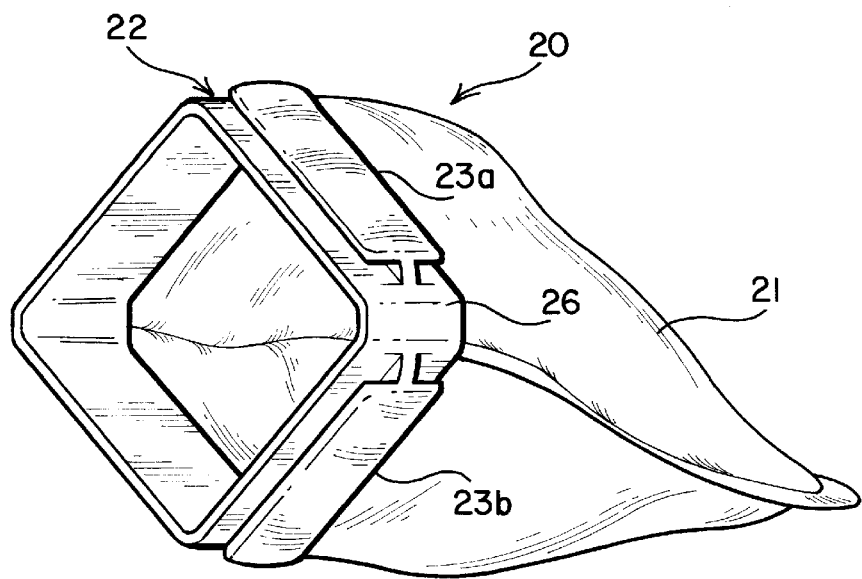
FIG. 4 is a perspective view of the bag in an open position.

Referring now to the drawings, FIG. 1 depicts a manipulating instrument or grasper 10 with jaws 11 and 12 in an open position. Each of the limbs 13 and 14 pivot about hinge 15 into an angle of approximately 45° which is required to expand the retrieval bag 20 into the configuration shown in FIG. 4. The grasper 10 is reusable while the retrieval bag assembly 20 is disposable.

FIG. 2 shows the bag assembly 20 in a closed position with the flexible plastic bag portion 21 located between the upper and lower portions 24a and 24b of the rigid plastic rim 22. The retrieval bag 20 includes raised portions 23a–d extending outwardly from the surfaces 24a and 24b with a recess or discontinuity 26 between adjacent raised portions 23a, 23b and 23c, 23d. The discontinuity 26 forms the corners of the bag 20 when it is expanded to the configuration of FIG. 4.

Figure 6:
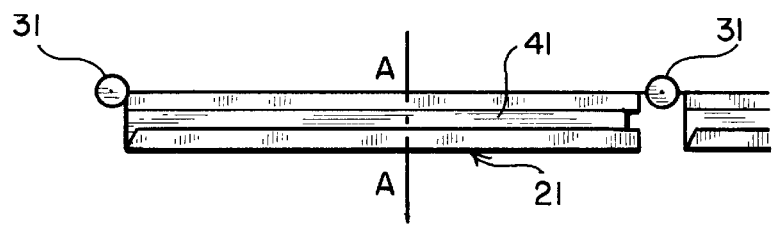
FIG. 6 is side view of the hinged embodiment of the invention.
Figure 5:
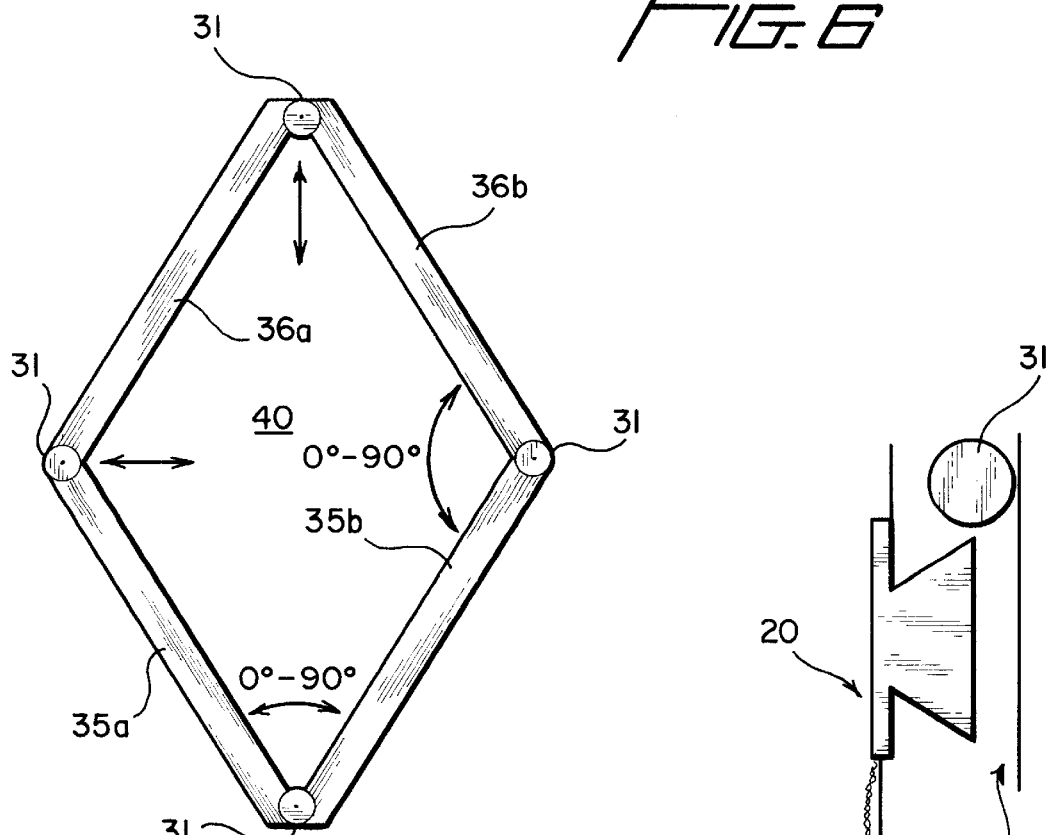
FIG. 5 is a schematic view showing the operation of the hinged limbs.

Substitution of the discontinuity 26 with hinges 31 as shown in FIGS. 5 and 6 will have the same effect. The grasper jaw limbs 13 and 14b open the hinges 31 causing the distal limbs 36a and 36b to spread apart along with limbs 35a and 35b forming the bag opening 40. The bag 21 is stored in the recess 41 in the rim 22.

FIG. 3 depicts the manipulating instrument 10 and retrieval bag assembly 20 assembled together snugly in a closed position. The flexible bag portion 21 is rolled within the rim 22. The limbs 13 and 14 of instrument 10 engage the raised portions 23b and 23c of the bag 20 so that spreading the limbs 13, 14 as shown in FIG. 1 causes the rim 22 to expand into a essentially hollow square configuration so that organs can be deposited therethrough into the flexible bag portion 21.

Different sizes of bags 21 can fit onto the same manipulating instrument 10 providing a versatility which does not exist with the prior art. This permits use of an appropriate size bag 21 for the particular organ being removed. The collapsible assembly system shown and described above permits the insertion into body cavities and subsequent expansion to retrieve organs. Also, the bag assembly 20 can be opened and closed at will as desired to maintain the organs in the plastic bag portion 21.

Figure 7:
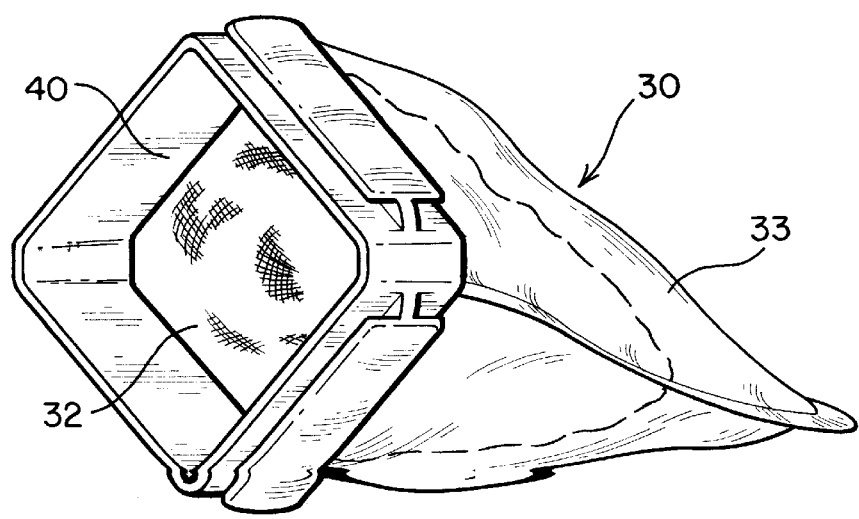
Figure 6A:
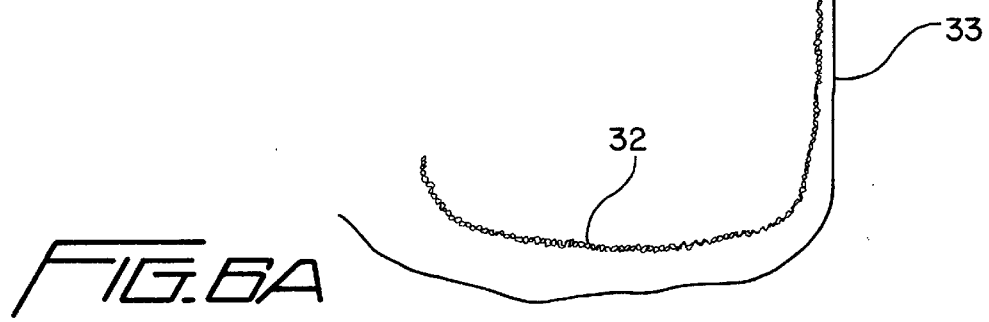
FIG. 6a is a cross-sectional view taken along the line A—A of FIG. 6 showing the inner and outer retrieval bags; and, FIG. 7 is a perspective view of the unique two layer retrieval bag in an open position.

FIGS. 6, 6A and 7 illustrate the unique two layer retrieval bag 30. The bag 30 comprises an inner mesh bag 32 an outer waterproof plastic bag 33. The smaller resilient mesh inner bag 32 permits fluids from the removed organs to drain into the outer bag 33. This facilitates removal of the organs or tissues through the port (not shown) without disruption.

While the invention has been explained by a detailed description of certain specific embodiments, it is understood that various modifications and substitutions can be made in any of them within the scope of the appended claims which are intended also to include equivalents of such embodiments.

What is claimed, is:

1. An endoscopic retrieval bag for organs and tissues bag system comprises:

a grasper including a pair of jaws each having an elongated limb extending outwardly therefrom and a hinge pivotally mounting the jaws together; and, a retrieval bag assembly comprising a closed collapsible rim mounted on the elongated grasper limbs and a retrieval bag for organs and tissues mounted within said rim wherein the rim when open comprises a substantially rectangular hollow structure having four sides and said rim is mounted on the limbs of the grasper such that activation of the grasper opens the rim to receive organs and tissues within the retrieval bag.

2. An endoscopic retrieval bag for organs and tissues bag system in accordance with claim 1 wherein:

the rim includes raised portions along the sides thereof and a recessed portion joining two adjacent sides to form the corners of a rectangle when the grasper opens.

3. An endoscopic retrieval bag for organs and tissues bag system in accordance with claim 2 wherein:

the bag comprises an elongated flexible bag mounted to the rim.

4. An endoscopic retrieval bag for organs and tissues bag system in accordance with claim 2 wherein:

the bag comprises an inner bag with a resilient mesh inner layer and an outer bag with a water proof plastic outer layer wherein the inner bag permits fluids from the removed organs and tissues to drain into the outer plastic bag.

5. An endoscopic retrieval bag for organs and tissues bag system in accordance with claim 1 wherein:

the rim includes a hinge at each corner mounted to the ends of adjacent sides.

6. An endoscopic retrieval bag for organs and tissues bag system in accordance with claim 1 wherein:

the grasper jaws open to an angle of 45° forcing the rim assembly into a rectangular structure.

7. An endoscopic retrieval bag for organs and tissues bag system in accordance with claim 1 wherein:

the grasper is reusable and the retrieval bag is disposable.

8. An endoscopic retrieval bag for organs and tissues bag system in accordance with claim 1 wherein:

retrieval bags of different sizes may be mounted to the rim.

9. An endoscopic retrieval bag system in accordance with claim 1 wherein:

both the grasper and retrieval bag assembly are disposable.

10. An endoscopic retrieval bag system in accordance with claim 1 wherein:

the retrieval bag assembly can open and close repeatedly at will for sequential deposit of elements, tissues or organs to be extracted.

* * * * *